United States Patent [19]

Lovelace

[11] 4,034,049

[45] July 5, 1977

[54] MO CATALYZED CHLORINATION OF DICHLOROBUTENES

[75] Inventor: Billy J. Lovelace, Houston, Tex.

[73] Assignee: Petro-Tex Chemical Corporation, Houston, Tex.

[22] Filed: Nov. 19, 1975

[21] Appl. No.: 633,379

[52] U.S. Cl. .......................... 260/658 R; 252/441; 252/437; 252/439
[51] Int. Cl.² .......................................... C07C 17/02
[58] Field of Search ................................ 260/658 R

[56] References Cited

UNITED STATES PATENTS

| | | | |
|---|---|---|---|
| 2,445,729 | 7/1948 | Radcliffe et al. | 260/660 |
| 2,560,025 | 7/1951 | Eberly et al. | 260/658 R |
| 3,932,544 | 1/1976 | Lovelace | 260/658 R |

Primary Examiner—D. Horwitz
Attorney, Agent, or Firm—Kenneth H. Johnson; N. Elton Dry

[57] ABSTRACT

Meso-1,2,3,4-tetrachlorobutane is produced in an improved liquid phase chlorination process wherein the trans-1,4-dichlorobutene-2 is contacted with chlorine in the presence of a catalytic amount of molybdenum.

22 Claims, No Drawings

MO CATALYZED CHLORINATION OF DICHLOROBUTENES

BACKGROUND OF THE INVENTION

The present invention relates to a process for the preparation of meso-1,2,3,4-tetrachlorobutane by chlorination of trans-1,4-dichlorobutene-2. More particularly the present invention relates to a catalytic chlorination process in liquid phase.

2,3-dichloro-1,3-butadiene, which is a valuable monomer used for polymerizations, e.g., the copolymerization with chloroprene (2-chloro-1,3-butadiene) to produce crystallization resistant types of rubber is conveniently made by the dehydrochlorination of meso-1,2,3,4-tetrachlorobutane. Although the 2,3-dichloro-1,3-butadiene may be made from the dl-racemic mixture of 1,2,3,4-tetrachlorobutane the meso-isomer produces higher yield and fewer undesirable by-products.

In preparing meso-1,2,3,4-tetrachlorobutane from dichlorobutenes in a liquid phase chlorination process, there are produced, in addition to the desired meso-isomer, dl-isomer and a proportion of chlorinated materials designated as heavy ends and light ends. These heavy ends are generally more highly chlorinated products such as the pentachlorobutanes. The light ends are less chlorinated products such as the trichlorinated $C_4$'s. The formation of dl-isomer and heavy and light ends is undesirable in that these materials represent a yield loss and are undesirable contaminants in the desired meso-1,2,3,4-tetrachlorobutane product.

Known methods for preparing meso-1,2,3,4-tetrachlorobutane from dichlorobutenes in a liquid phase chlorination process have been generally unsatisfactory. Non-catalytic process, such as those disclosed in Japanese Pat. No. 38,802 (1970) and in the Journal of the American Chemical Society 73, 244-6 (1951), require extremely low temperatures of from 0° C. to about −30° C. and are, therefore, generally undesirable economically. Other processes for carrying out the chlorination reaction at moderate temperatures in the range of from about 50° C.–150° C. involve the use of a catalyst, for example, the processes disclosed in French Pat. No. 1,401,077 (titanium tetrachloride catalysts), French Pat. No. 1,401,078 (pyridine catalysts), and U.S. Pat. No. 2,445,729 (ferric chloride or antimony pentachloride catalysts). All of these processes are generally unsatisfactory in that there are produced a large proportion of heavy ends material and an undesirably large proportion of the dl-isomer. These catalytic processes are additionally undesirable due to the presence of the metallic catalyst.

Recently improved processes have been described in U.S. Pat. No. 3,901,950 (oxygen and dissolved chloride ion), U.S. Pat. No. 3,980,725 (absence of oxygen in the presence of nitric oxide) and U.S. Pat. No. 3,932,544 (controlled chlorine reaction rate), all of which have succeeded in reducing the dl-isomer in the chlorination reaction.

The light ends represent lost production of the desirable tetrachlorbutane, i.e., particularly the desirable meso-isomer.

The advantages of the present invention include reduced light ends from the chlorination of trans-1,4-dichlorobutene-2; improved reaction rate time trends; lower heavy ends and increased yield of meso-1,2,3,4-tetrachlorobutane. A particular feature of the present invention is that the present catalyst may be used in combination with other improvement in the art.

SUMMARY OF THE INVENTION

Briefly stated the present invention is a liquid phase process for the chlorination of trans-1,4-dichlorobutene-2 in the presence of a catalytic amount of molyldenum. In the presence of molybdenum in the reaction, the amount of light ends has been reduced and higher yields of meso-1,2,3,4-tetrachlorobutane are obtained.

DETAILED DESCRIPTION OF THE INVENTION

General Reaction Conditions

In carrying out the present chlorination it is desirable that there be provided in the reaction zone suitable means for agitating the liquid reaction mass to facilitate the contact of the chlorine or chlorine-containing gas with the dichlorobutenes. Agitation of the reaction mixture also insures that there is a good distribution of chlorine throughout the reaction mixture and that undesirably high chlorine concentrations are thereby avoided. Any number of agitator means are suitable, as will be apparent to one skilled in the art. For example, it has been found useful to employ propeller driven agitators, turbine blades, orifice mixing devices, inert gas spargers, and various baffle arrangements in the reaction zone.

The temperature at which the chlorination reaction of this invention is carried out is not critical and can vary over wide limits. It has been found that satisfactory results are obtained whenever the chlorination reaction as described herein is carried out at temperatures of from about 25° C. to about 150° C. A preferred temperature range for conducting the chlorination of 1,4-trans-dichlorobutene-2 is from about 50° C. to about 100° C. The pressure at which the process of this invention is conducted is, likewise, not critical and can vary over rather wide limits. As a general proposition, the higher the reaction pressure selected, the higher the rate at which the chlorine is dissolved into the liquid reaction medium. Suitable reaction pressures can include subatmospheric pressure, atmospheric pressure or superatmospheric pressure. Generally, however, subatmospheric pressure is avoided because of the concomitant problems associated with the leakage of oxygen into the reaction system. Preferred reaction pressures are within the range of about 15 psia to about 100 psia, with reaction pressures of from about 15 psia to about 50 psia being especially preferred.

The chlorination reaction of the process of this invention is carried out in a reaction zone wherein the liquid dichlorobutene-containing feedstock is contacted with chlorine. The manner by which the contacting is effected can vary depending upon other parameters of the process. Chlorine may be introduced into the gas envelope above the liquid dichlorobutene in a reactor vessel designed for batch chlorinations. The chlorination reaction takes place as the chlorine dissolves into the dichlorobutene reactant in the reactor vessel. The addition of chlorine to the reaction zone is continued until all or a desired amount of the dichlorobutene starting materials have been chlorinated to products. In an alternate embodiment, chlorine is introduced directly into the liquid dichlorobutene reactants, generally by means of a nozzle or plurality of nozzles. Again, the chlorine addition continues until the desired level of chlorination has been effected. In continuous processes, such as where the dichlorobutene reactants are flowing through a tubular reactor, provision can be made for the staged addition of chlorine into the reactor system at a plurality of points.

It is preferred that the manner in which the contacting of the dichlorobutenes and chlorine is effected is such that the chlorine concentration is maintained at as low a concentration as is practicable, since high concentrations of chlorine tend to promote the formation of higher chlorinated derivatives.

Since the reaction of chlorine with the olefinic materials present in the reaction zone is generally a relatively fast reaction, the relatively low chlorination rates which are the object of this invention are obtained by adjustment of the rate at which chlorine is introduced into the reaction zone at a rate of from about 0.01 to about 2.0 mol percent per minute based upon the amount of dichlorobutenes initially present. Preferably, the chlorine addition rate will be from about 0.1 to about 1.0 mol percent per minute, based upon the dichlorobutenes initially present.

The determination of an optimum chlorine addition rate within the aforementioned ranges will depend, in part, upon the manner in which the chlorine is introduced into the reaction zone, i.e., chlorine through a nozzle or plurality of nozzles extending into the liquid reactants or into the gas space above the liquid dichlorobutene reactants. In either embodiment, the addition of chlorine into the reaction zone is continued until the desired amount of the dichlorobutene starting materials have been chlorinated to products. Generaly, the introduction of chlorine into the reaction zone in the gas space above the dichlorobutene reactants results in less production of heavy ends. Also, the lower the addition rate of chlorine into the reaction zone, the higher the proportion of meso-isomer produced and the lower the proportion of heavy ends produced.

In embodiments of this invention in which the chlorination is effected in a batch process, the chlorine addition rate ideally is a function of time; the chlorine addition rate may be gradually reduced to maintain the desired low chlorination rate as, the dichlorobutenes are converted to tetrachlorobutanes. However, it is equivalently useful to select an initial chlorine addition rate which results in a desirably low chlorination rate and to maintain this chlorine addition rate throughout the chlorination reaction period. Such a uniform chlorination rate additionally facilitates the maintenance of a uniform reaction zone temperature. Depending upon desired crude product specifications, the chlorine addition can be terminated prior to the chlorination of all of the dichlorobutenes present so as to avoid the high chlorine to dichlorobutene ratios. The unreacted dichlorobutenes can then be recovered and recycled to the reaction zone and be subsequently chlorinated to desired product.

In a continuous chlorination reaction process according to this invention, the relatively low chlorination rates are maintained by staged chlorine addition. That is, continuous addition of chlorine at a plurality of addition points located along the reaction zone. The chlorine addition rate at each of the plurality of chlorine addition locations can be the same or can decrease in rate in the downstream direction of the reaction zone as the dichlorobutene contact of the reaction mixture decreases.

In the instant invention, chlorine can be introduced into the reaction zone as chlorine gas or as chlorine gas in admixture with a diluent gas which is inert to the reaction environment. Suitable diluent gases include the inert gases such as helium and argon; nitrogen; and saturated lower alkanes such as methane and ethane.

The total amount of chlorine required to effect the desired degree of chlorination in the process of this invention will depend upon the manner in which chlorine is introduced into the reaction zone. Stoichiometrically, one mol of chlorine is required for each mol of meso-1,2,3,4-tetrachlorobutane to be produced from the dichlorobutene starting materials. Generally, however, a slight excess of chlorine will be required to effect the desired degree of chlorination. In batch chlorinations wherein chlorine is introduced in admixture with an inert gas into the gas space of the reaction zone as hereinbefore described, a greater excess of chlorine will be required to effect a given level of chlorination than in the case of a batch chlorination wherein the chlorine alone is introduced directly into the liquid dichlorobutene reactant. However, the amount of excess chlorine required is generally not large and can, in any event, generally be recovered from the reaction zone and recycled for reuse.

In a preferred embodiment of the process of the instant invention, the chlorination reaction described herein is carried out in the additional presence of an effective amount of nitric oxide. By effective amount is meant that quantity of nitric oxide necessary to effectively suppress the formation of the undesirable dl-isomer and the higher chlorinated derivatives.

An effective amount can be readily determined by one skilled in the art without undue experimentation. The reaction zone configuration and the manner of addition of nitric oxide will, in part, determine what constitutes an effective amount of nitric oxide, as will hereinafter become apparent.

Nitric oxide is provided to the reaction zone so as to be present during the contacting of the dichlorobutenes with chlorine. The nitric oxide preferably is present in the reaction zone both in the liquid dichlorobutene-containing reaction mixture and in the gas envelope of the reaction zone above the liquid reaction mixture. It is introduced into the reaction zone prior to addition of the chlorine, is introduced continuously during the chlorination reaction, or both. Also, the nitric oxide can be added as nitric oxide or in admixture with an inert gas. Nitric oxide is added to the reaction zone in a gas purge wherein nitric oxide and an inert gas, such as nitrogen, are introduced into the bottom of the reaction zone in the liquid dichlorobutene-containing mixture. The purging action is continued until the reaction zone is free of oxygen and there is sufficient nitric oxide remaining in the reaction zone to effect the desired suppression of the formation of dl-isomer and heavy ends as hereinbefore described. Generally, such a purging action requires from about 2 to about 20 reactor volumes of purging gas and will result in there being from about 0.1 to about 20 mol percent nitric oxide present in the reaction zone, based on the amount of trans1,4-dichlorobutene-2 present. Thereafter, chlorine is introduced into the reaction zone and the chlorination reaction is begun. In one embodiment, nitric oxide addition to the reaction zone is continued after the initial purging operation and is maintained throughout the course of the chlorination reaction. When nitric oxide is provided solely by the initial gas purging operation, a nitric oxide concentration of from about 1 to about 20 mol percent, based on the inert gas, is satisfactory. Preferably, the reaction system is purged with an inert gas until substantially free of oxygen and then the purging operation is continued for a suitable period with the additional presence of nitric oxide in the purging gas. Where nitric oxide is added continuously throughout the course of the chlorination reaction, nitric oxide addition rates of from about 0.1 to about 10% by volume based on the chlorine addition rate are satisfactory, with a nitric oxide addition rate of from about 0.5 to about 5% being preferred.

Reaction Feeds

The feedstocks useful in practicing the instant invention are trans-1,4-dichlorobutene-2 and 3,4-dichlorobutene-1. These compounds are generally available in mixtures containing other chlorinated compounds such as, for example, cis-1,4-dichlorobutene-2 and the trichlorobutenes. The presence of these materials is not deleterious to the process of the instant invention; however, concentrations of such compounds should be kept to a minimum inasmuch as they are chlorinated to products other than meso-1,2,3,4-tetrachlorobutane.

The preferred feedstock for practicing this invention is trans-1,4-dichlorobutene-2 since the tetrachloro product from the chlorination of this feedstock is substantially all meso-1,2,3,4-tetrachlorobutane. However, the chlorination of 3,4-dichlorobutene-1 also results in the production of meso-1,2,3,4-tetrachlorobutane; therefore, either trans-1,4-dichlorobutene-2,3,4-dichlorobutene-1, or mixtures thereof are useful in practicing the instant invention.

Although the process of the instant invention can be carried out in the absence of any solvent, it is equivalently useful to provide a solvent for the reactants. Suitable solvents generally include halogenated solvents such as methylene chloride, chloroform, carbon tetrachloride, and certain halogenated aromatic solvents such as chlorobenzene. Whenever a solvent is employed in the process of the instant invention, the amount is not critical and can vary. Solvent concentrations of from about 10 to about 90 wt.% are satisfactory, with concentrations of from about 25 to about 75 wt.% being preferred.

After the reaction, the unreacted chlorine is generally removed from the crude product mixture and the desired meso-1,2,3,4-tetrachlorobutane produce is thereafter recovered by conventional means, such as by fractional distillation, selective extraction, fractional crystallization and the like. Unreacted dichlorobutenes are recovered and recycled for further reaction according to the process of this invention. The meso-1,2,3,4-tetrachlorobutane is generally recovered in high purity from the crude product containing both the dl-and meso-isomers by conventional fractional crystallization techniques. The remaining small proportion of trichloro compounds, generally present in the reaction mixture, may be recovered as a separate product.

Catalyst

According to the present invention a catalytic amount of molybdenum is employed. The term "catalytic amount" as used herein is meant that amount of molybdenum necessary to effectively increase the degree of chloration of lower chlorinated derivatives.

Generally the catalytic amount of molybdenum employed is quite small only from about 100 to 1000 parts per million (PPM) by weight based on the weight of starting dichlorobutenes is necessary, preferably about 200 to 500 PPM of molybdenum will be present in the reaction on the same basis.

The molybdenum is present in solution as a homogenous catalyst, hence generally soluble compounds of molybdenum including both organic and inorganic salts may be employed.

The catalysts are suitably added as compounds of molybdenum; it is possible, however, to add the catalyst as finely divided metal with the metal being eventually converted to a compound sufficiently soluble to provide a catalytic amount of the metal in solution in the reaction mixture. The catalysts remain dissolved in the reaction mixture throughout the process and can be reused in the reaction after removal of the reaction products therefrom. The molybdenum compounds include the molybdenum organic salts, the oxides such as $Mo_2O_3$, $MoO_2$, molybdic acid the molybdenum chlorides and oxychlorides, molybdenum fluoride, phosphate, sulfide, and the like. Hetero-polyacids containing molybdenum can be used as can salts thereof; examples include phosphomolybdic acid and the sodium and potassium salts thereof.

The catalytic components may be employed in the chlorination reaction in the form of a compound or mixture which is initially soluble in the reaction medium. Solubility will, to some extent depend on the particular reaction medium employed. Illustrative forms of the catalytic materials are the stearates, octoates, carbonyls and the like. Various chelates, association compound and enol salts, such, for examples, as aceto-acetonates may also be used. Specific and preferred catalytic compounds of this type for use in the invention are the acetoacetonates of molybdenum.

Since such minute quantities of catalyst are employed contamination of the product is not a problem.

A particularly preferred group of catalysts are $MoCl_5$, $MoCl_4$, $MoCl_3$, $MoOCL_4$ or $MoOCl_3$.

EXAMPLES 1-7

These Examples illustrate the effect of carrying out the chlorination of trans-1,4-dichlorobutene in the added presence of molybdenum. Examples 1 and 4 serve as controls. In each of the runs reported in the Table, the feedstock was charged into a 1-litter, 3-necked flask equipped with a water jacket for cooling and an agitator means. The reaction flask in each case was then purged of oxygen using a stream of gas. In Examples 1 and 6 the chlorine was introduced into the dichlorobutene reaction mixture via a 4-mm. nozzle positioned below the liquid level of the reaction flask to effect the chlorination. In all other examples the chlorine was introduced into the vapor space above the dichlorobutene reaction mixture. The chlorination reaction was carried out with nitric oxide being added continuously to the reactor vessel along with the chlorine, maintained at a rate which resulted in the indicated chlorination rates. The temperature of the reaction mixture was maintained at approximately 70° C. by adjustment of the cooling water flow through the water jacket surrounding the reaction flask. The end of the chlorination reaction was determined to be that point at which the indicated temperature began to decrease. Data from these runs are in the following Table.

At the end of the reaction period, the product was worked up as follows. A heating medium was substituted for the cooling water in the water jacket and the temperature of the reaction flask contents was maintained at 70° C. The reaction flask was then purged with nitrogen to degas the system of the residual chlorine. Throughout the purging, the contents of the reaction flask were stirred to liberate any entrained chlorine. A sample from the reaction flask was dissolved in dichloromethane and analyzed by gas chromatographic techniques to yield the above analysis. The remaining contents of the reaction flask were then diluted with approximately one-half its volume of isopropyl alcohol. The mixture was then stirred rapidly and allowed to cool to 20°-26° C. At this temperature, crystallization of the meso-1,2,3,4-tetrachlorobutane was effected. The crystals, after filtering, washing, and drying analyzed 99+ wt.% meso-1,2,3,4-tetrachlorobutane.

TABLE

| EXAMPLE | 1 | 2 | 3 | 4 | 5 | 6 | 7 |
|---|---|---|---|---|---|---|---|
| Feed Composition (Area %)**** | | | | | | | |
| 3,4-dichlorobutene-1 | 2.2 | 2.2 | 2.2 | 0.5 | 0.5 | 2.2 | 2.2 |
| cis-1,4-dichlorobutene-2 | 4.1 | 4.1 | 4.1 | 7.7 | 7.7 | 4.1 | 4.1 |
| trans-1,4-dichlorobutene-2 | 93.3 | 93.3 | 93.3 | 89.0 | 89.0 | 93.3 | 93.3 |
| Heavy ends | 0 | 0 | 0 | 2.5 | 2.5 | 0 | 0 |
| Feed charged, grams | 252 | 273 | 275 | 366 | 289 | 299 | 307 |
| N$_2$/NO Gas Purge* | yes | yes | yes | yes | yes | yes | yes |
| Chlorination Temp., ° C. | 70 | 70 | 70 | 70 | 70 | 70 | 70 |
| Chlorination rate | | | | | | | |
| Mol DCB chlorinated/hr | 1.0 | 1.5 | 1.3 | 1.4 | 1.5 | 1.3 | 1.4 |
| Continuous NO Addition** | yes | yes | yes | yes | yes | no | no |
| Mol Cl$_2$/100 mol DCB/min*** | >2.0 | 1.9 | >1.9 | 1.0 | 1.3 | (0.92) | (0.92) |
| Catalysts (ppm, as Mo) | None | | | None | | | |
| MoCl$_4$ | — | 230 | 360 | — | | 200 | 375 |
| Molybdenyl bis-acetylacetonate | — | — | — | — | 200 | — | — |
| Product Composition (Area %)**** | | | | | | | |
| Unreacted DCB | 0.8 | 0 | 0 | 0 | 0 | 0 | 0 |
| Light ends | 7.6 | 3.6 | 3.7 | 8.3 | 6.1 | 3.6 | 2.1 |
| dl-1,2,3,4-tetrachlorobutane | 6.4 | 7.0 | 8.4 | 8.7 | 9.8 | 7.2 | 6.7 |
| meso-1,2,3,4-tetrachlorobutane | 84.8 | 88.2 | 87.2 | 81.4 | 82.8 | 88.0 | 88.4 |
| Heavy ends | 0.2 | 1.1 | 0.4 | 1.5 | 1.3 | 0.4 | 1.7 |

*1000 ml/min nitrogen and 100 ml/min nitric oxide sparged through reaction zone for 5 minutes.
**Approximately 10ml/min.
***Values in parentheses are calculated from chlorination rates.
****Gas chromatographic area %.

From the above data in the Table, it is apparent that carrying out the chlorination in the presence of molybdenum has a substantial effect on the chlorination of the light ends and favoring the meso-isomer in the isomer distribution produced.

From the foregoing description and examples which are illustrative and not limiting of the present invention, those of ordinary skill in the art may make many modifications and variations therefrom without departing from the scope of the invention as hereinafter claimed.

The invention claimed is:

1. In a process for the production of meso-1,2,3,4-tetrachlorobutane by contacting in a reaction zone trans-1,4-dichlorobutene-2 in the liquid phase with chlorine at a temperature of from about 25° C. to about 150° C. in the substantial absence of oxygen, the improvement which comprises:
effecting said contacting of trans-1,4-dichlorobutene-2 and chlorine in the presence of a catalytic amount of molybdenum.

2. The process according to claim 1 wherein molybdenum is added to the reaction zone as a compound soluble in said liquid phase.

3. The process according to claim 1 wherein molybdenum compound is added to the reaction zone in an amount of from about 100 to about 1000 parts per million by weight determined as molybdenum and based on the trans-1,4-dichlorobutene-2.

4. The process according to claim 3 wherein said molybdenum compound is MoCl$_5$, MoCl$_4$, MoCl$_3$, MoOCl$_4$ or MoOCl$_3$.

5. The process according to claim 3 wherein said molybdenum compound is MoCl$_4$.

6. The process according to claim 3 wherein said molybdenum compound is molybdenyl bis-acetylacetonate.

7. The process according to claim 3 wherein said molybdenum is added to said reaction zone in amount of 200 to 500 parts per million by weight determined as molybdenum and based on the trans-1,4-dichlorobutene-2.

8. The process to claim 1 wherein nitric oxide is added to the reaction zone in an amount of from about 0.1 to about 20 mol precent based on trans-1,4-dichlorobutene-2.

9. The process according to claim 8 wherein the nitric oxide is introduced into the reaction zone prior to said contacting of the trans-1,4-dichlorobutene-2 and the chlorine.

10. The process according to claim 8 wherein the nitric oxide is introduced into the reaction zone during said contacting of the trans-1,4-dichlorobutene-2 and the chlorine.

11. The process according to claim 10 wherein the nitric oxide is further continuously introduced during the contacting of the trans-1,4-dichlorobutene-2 and the chlorine in an amount of from about 0.1 to about 10 volume percent based on the volume of chlorine.

12. The process according to claim 11 wherein said contacting is effected by introducing the chlorine into the gas space of the reaction zone containing the liquid trans-1,4-dichlorobutene-2 whereby the chlorine dissolves into the trans-1,4-dichlorobutene-2 at the liquid-gas interface in the reaction zone.

13. The process according to claim 11 wherein said contacting is effected by introducing the chlorine into the liquid trans-1,4-dichlorobutene-2-containing reaction mixture.

14. The process according to claim 11 wherein the chlorine is introduced into the reaction zone containing the trans-1,4-dichlorobutene-2 at a rate of from about 0.01 to about 2.0 mol percent per minute based on the amount of trans-1,4-dichlorobutene-2 initially present, for a period of time sufficient to effect the desired chlorination of the trans,-1,4-dichlorobutene-2.

15. The process according to claim 14 wherein said contacting is effected by introducing the chlorine into the gas space of the reaction zone containing the liquid trans-1,4-dichlorobutene-2.

16. The process according to claim 14 wherein said contracting is effected by introducing the chlorine into the liquid trans-1,4-dichlorobutene-2 containing reaction mixture.

17. The process according to claim 1 wherein said contacting of trans-1,4-dichlorobutene-2 in the liquid phase with chlorine is at a temperature from about 50° to 100° C. said contacting being effected in the presence of an effective amount of nitric oxide.

18. The process according to claim 17 wherein nitric oxide is continuously introduced during the contacting of trans-1,4-dichlorobutene-2 and chlorine.

19. The process according to claim 18 wherein nitric oxide is added at rates of from about 0.1 to about 10% by volume based on the chlorine addition rate.

20. The process according to claim 19 wherein the rates of nitric oxide addition are from about 0.5 to about 5%.

21. The process according to claim 17 wherein nitric oxide is introduced into the reaction zone prior to said contacting of trans-1,4-dichlorobutene-2 and the chlorine.

22. The process according to claim 21 wherein nitric oxide is further continuously introduced into said reaction zone during the contacting of the trans-1,4-dichlorobutene-2 and chlorine in an amount of from about 0.1 to about 10 volume percent based on the volume of chlorine.

* * * * *